United States Patent
Michalak

(10) Patent No.: US 11,458,007 B2
(45) Date of Patent: Oct. 4, 2022

(54) DEVICES AND METHODS FOR LIMITING A DEPTH OF PENETRATION FOR AN ANCHOR WITHIN AN ANATOMY

(71) Applicant: W. L. Gore & Associates, Inc., Newark, DE (US)

(72) Inventor: Christopher S. Michalak, Elkton, MD (US)

(73) Assignee: W. L. Gore & Associates, Inc., Newark, DE (US)

( * ) Notice: Subject to any disclaimer, the term of this patent is extended or adjusted under 35 U.S.C. 154(b) by 108 days.

(21) Appl. No.: 13/961,416

(22) Filed: Aug. 7, 2013

(65) Prior Publication Data

US 2014/0046427 A1   Feb. 13, 2014

Related U.S. Application Data

(60) Provisional application No. 61/681,677, filed on Aug. 10, 2012.

(51) Int. Cl.
*A61F 2/06* (2013.01)
*A61F 2/07* (2013.01)
*A61F 2/848* (2013.01)

(52) U.S. Cl.
CPC ............... *A61F 2/064* (2013.01); *A61F 2/07* (2013.01); *A61F 2/848* (2013.01);
(Continued)

(58) Field of Classification Search
CPC .. A61F 2/848; A61F 2/064; A61F 2/07; A61F 2002/8483; A61F 2002/8486;
(Continued)

(56) References Cited

U.S. PATENT DOCUMENTS 4,562,596 A    1/1986  Kornberg
5,059,205 A *  10/1991 El-Nounou et al. .......... 606/200
(Continued)

FOREIGN PATENT DOCUMENTS

EP   0701800 A    3/1996
EP   0896813 A2   2/1999
(Continued)

OTHER PUBLICATIONS

International Search Report and Written Opinion, PCT/US2013/054049, dated Nov. 8, 2013, 17 pages.
(Continued)

*Primary Examiner* — Katherine H Schwiker

(57) ABSTRACT

A medical securing device that includes (1) a pointed tip and (2) a depth stop is provided. The depth stop includes an apex portion coupled to a trough portion. The depth stop limits the depth of penetration of the pointed tip into a wall of a body lumen. In one or more embodiment, the medical securing device may be constructed from a length of shape memory wire. Thus, during deployment, the medical securing device may spring away from a medical device to which the medical securing device is coupled such that the pointed tip makes contact with and punctures, to a limited depth, a body lumen wall. In various embodiments, a pair of barbs may be coupled to from an integral two pronged barb.

21 Claims, 2 Drawing Sheets

(52) U.S. Cl.
CPC ............... *A61F 2002/8483* (2013.01); *A61F 2002/8486* (2013.01); *A61F 2220/0016* (2013.01)

(58) Field of Classification Search
CPC ...... A61F 2220/0016; A61F 2220/0008; A61F 2/89; A61F 2/01; A61F 2002/072; A61F 2002/075; A61F 2002/077; A61F 2002/016; A61F 2230/005; A61B 2220/0008; A61B 17/11; A61B 17/064; A61B 17/0644
USPC .............................. 623/1.12, 1.14, 1.32, 1.36
See application file for complete search history.

(56) References Cited

U.S. PATENT DOCUMENTS

| | | | |
|---|---|---|---|
| 5,108,418 A * | 4/1992 | Lefebvre | A61F 2/01 210/448 |
| 5,843,167 A * | 12/1998 | Dwyer | A61F 2/07 623/1.14 |
| 6,290,719 B1 * | 9/2001 | Garberoglio | 623/1.15 |
| 7,918,873 B2 | 4/2011 | Cummins | |
| 2003/0093117 A1 | 5/2003 | Saadat | |
| 2003/0220683 A1 | 11/2003 | Minasian | |
| 2004/0117004 A1 | 6/2004 | Osborne et al. | |
| 2005/0102024 A1 * | 5/2005 | Riccotta | A61F 2/07 623/1.23 |
| 2006/0253143 A1 | 11/2006 | Edoga et al. | |
| 2007/0093888 A1 | 4/2007 | Thistel | |
| 2008/0021544 A1 * | 1/2008 | Majercak et al. | 623/1.36 |
| 2008/0033534 A1 | 2/2008 | Cook et al. | |
| 2009/0048665 A1 * | 2/2009 | Miron | A61B 17/11 623/1.36 |
| 2009/0306681 A1 | 12/2009 | Del Nido et al. | |
| 2010/0121373 A1 | 5/2010 | Tekulve | |
| 2010/0234886 A1 | 9/2010 | Godin | |
| 2010/0274345 A1 | 10/2010 | Rust | |
| 2010/0324584 A1 * | 12/2010 | Shaw | 606/194 |
| 2011/0160527 A1 * | 6/2011 | Khamis et al. | 600/37 |
| 2011/0319980 A1 * | 12/2011 | Ryan | A61F 2/07 623/1.16 |
| 2012/0035708 A1 * | 2/2012 | Paul et al. | 623/1.16 |
| 2012/0277848 A1 * | 11/2012 | Roeder et al. | 623/1.13 |

FOREIGN PATENT DOCUMENTS

| | | |
|---|---|---|
| EP | 1880693 | 1/2008 |
| JP | 19960299456 A | 5/1998 |
| JP | 4078298 B2 | 2/2008 |
| RU | 2108070 C1 | 4/1998 |
| WO | 02085254 A1 | 10/2002 |
| WO | WO2004/016201 | 2/2004 |
| WO | 2008/033474 A2 | 3/2008 |
| WO | WO-2008077067 A2 | 6/2008 |

OTHER PUBLICATIONS

Supplementary European Search Report from European Application No. 13827979.9, dated Feb. 3, 2016, 7 pages.

International Preliminary Report on Patentability received for PCT Patent Application No. PCT/US2013/054049, dated Feb. 19, 2015, 11 pages.

\* cited by examiner

DEVICES AND METHODS FOR LIMITING A DEPTH OF PENETRATION FOR AN ANCHOR WITHIN AN ANATOMY

CROSS REFERENCE TO RELATED APPLICATIONS

This Application claims priority to U.S. Ser. No. 61/681,677 filed Aug. 10, 2012.

BACKGROUND

Field

The present disclosure generally relates to the field of medicine, and more particularly, to securing devices such as anchors and barbs for securing medical devices within an anatomy or body (e.g., a human body).

Discussion of the Related Art

A variety of medical devices have been developed for implantation within an anatomy or body (e.g., a human body). Many such devices are implantable within a body lumen (e.g., the vasculature and/or gastrointestinal tract ("GI tract") of a human body). For instance, devices like stents, grafts, and stent-grafts may be implanted within the vasculature and/or GI tract of a human body to reinforce, replace, and/or bridge a damaged, unhealthy, or otherwise diseased portion of a body lumen. These devices may thus, in certain instances, guide blood and/or other fluids through a lumen defined by a cylindrical interior surface. During implantation, however, it is often necessary to anchor such devices in place, so that they will not migrate away from a damaged or diseased portion of the anatomy they are intended to repair.

Although techniques have been developed to hold devices like those described above in place, these techniques may suffer from a variety of shortcomings. For instance, a securing device (such as a medical anchor or barb) may entirely penetrate a body lumen, such that a sharpened portion of the securing device is exposed to (and may damage) surrounding tissue. This may occur, for example, where a securing device comprises a barb intended to penetrate a lumen wall (e.g., the duodenal bulb of the intestinal wall). The barb may, in some circumstances, fully penetrate the lumen wall, which may cause damage to surrounding anatomy and/or open a leakage path into surrounding anatomy.

More suitable techniques for securing a medical device to an intended location are therefore desirable. For instance, a securing device capable of partial implantation in a lumen wall (e.g., such that a lumen wall is not fully punctured) is desirable.

SUMMARY

The present disclosure includes a securing device comprising, for instance, one or more barbs. A securing device may comprise a depth stop, which may itself comprise an apex portion coupled to a trough portion. A securing device may be constructed, in various embodiments, from a length of shape memory wire. Thus, during deployment, a securing device may spring away from a medical device to which the securing device is coupled such that the securing device makes contact with and punctures, to a limited depth, a body lumen wall. A securing device need not, however, fully puncture a body lumen wall. Rather, a depth stop may limit a puncture depth to a depth that does not endanger and/or subject tissue surrounding or external to the lumen wall to damage and/or bleeding or leakage from within the lumen.

In various embodiments, a pair of securing devices may be coupled to from an integral two pronged securing device.

BRIEF DESCRIPTION OF THE DRAWINGS

The features and advantages of the present disclosure will become more apparent from the detailed description set forth below when taken in conjunction with the drawings, wherein.

DETAILED DESCRIPTION OF THE ILLUSTRATED EMBODIMENTS

Figure 1A:
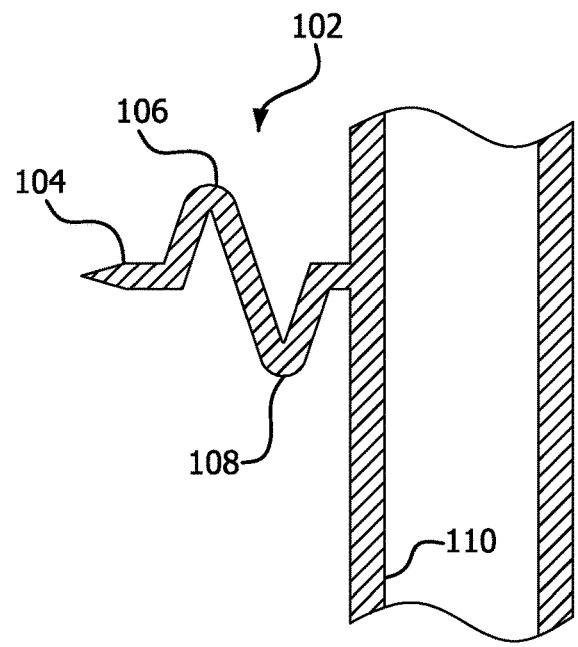
FIG. 1A illustrates a cross-sectional view of a securing device coupled to a medical device.

Persons skilled in the art will readily appreciate that various aspects of the present disclosure may be realized by any number of methods and apparatuses configured to perform the intended functions. Stated differently, other methods and apparatuses may be incorporated herein to perform the intended functions. It should also be noted that the accompanying figures referred to herein are not all drawn to scale, but may be exaggerated to illustrate various aspects of the present disclosure, and in that regard, the figures should not be construed as limiting. Finally, although the present disclosure may be described in connection with various principles and beliefs, the present disclosure should not be bound by theory.

As used herein, the phrase "securing device" may refer to a device capable of securing a medical device within a human body. For example, in various embodiments, a securing device may comprise an anchor, a staple, a clip, a hook, a tack, a barb, and the like.

Likewise, as used herein, the phrase "medical device" may refer to a device capable of being secured within a human body. For example, in various embodiments, a medical device may comprise a stent, a graft, a stent-graft, and the like.

While the specific embodiments are described in greater detail below, in general, the present disclosure will focus primarily upon devices and methods for securing a medical device within a body (e.g., a human body). For instance, in various embodiments, these devices and methods may be applied to treat diseases of the vasculature and/or GI tract, including any disease where a body lumen is implanted with a medical device.

In addition, although the devices and methods described herein may focus on application of a medical device to a human body, these devices and methods may be more broadly applied to secure medical devices within any part of any body (human, mammalian, or otherwise). Moreover, although the disclosure provided herein may focus, in part, upon embodiments in which a medical device is secured to a body lumen, the devices and methods described herein may apply equally to tissue to tissue fixation as well as to fixation of medical devices to non-luminal body tissue.

In various embodiments, a securing device (e.g., a securing device comprising one or more anchors or barbs) is disclosed. A securing device may comprise a depth stop, and a depth stop may, in turn, comprise an apex portion coupled to a trough portion. A securing device may be constructed, in various embodiments, from a length of shape memory wire. Thus, during deployment, a securing device may spring away from a medical device to which the securing device is coupled such that the securing device makes contact with and punctures, to a limited depth, a body lumen wall. A securing device may not, however, fully puncture a body lumen wall. Rather, a depth stop may limit a puncture depth to a depth that does not endanger and/or subject tissue surrounding or external to the lumen wall to damage and/or bleeding or leakage from within the lumen.

With reference now to FIG. 1A, a cross-sectional view of a securing device 102 is shown. A securing device 102 may comprise a depth stop, which may limit a depth of penetration of the device 102 into a body lumen. A securing device 102 may further comprise a pointed tip 104, which may be coupled to a depth stop. In various embodiments, a depth stop may comprise an apex or ridge portion 106 coupled to a trough or depression portion 108. Thus, in various embodiments, a depth stop may comprise an undulating shape, such as an "S" or zigzag shape, a mirror image of an "S" or zigzag shape, and the like. A securing device 102 may be coupled to a medical device (e.g., a stent or stent-graft) 110, as shown.

Figure 1B:
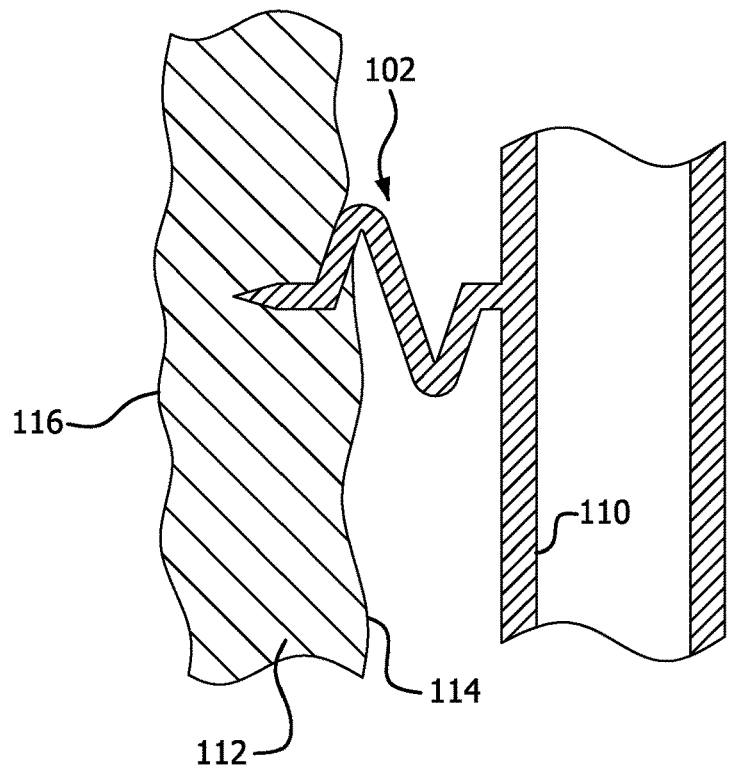
FIG. 1B illustrates a cross-sectional view of a securing device coupled to a medical device and engaged with a body lumen wall.

With reference now to FIG. 1B, a cross-sectional view of a securing device 102 penetrating a body lumen wall 112 is shown. As depicted, a securing device 102 may secure and/or stabilize a medical device 110 as the medical device 110 engages a body lumen wall 112. Further, a depth stop of a securing device 102, as described above, may limit a depth of penetration of the securing device 102 into the body lumen wall 112. More particularly, in various embodiments, a ridge portion 106 and/or a trough portion 108 of a depth stop may, individually and/or together, limit a depth of penetration of a securing device 102 into a body lumen wall 112. For example, a securing device 102 may encounter resistance as the ridge portion 106 and/or the trough portion 108 engage or make contact with a luminal surface 114 of the body lumen wall 112 sufficient to halt further penetration of the securing device 102 into the body lumen wall 112. Thus, the undulating shape of a depth stop may, as shown, prevent a securing device 102 from fully puncturing a body lumen wall 112. Rather, the progress of the pointed tip 104 of a securing device 102 may be halted by a depth stop in its progress through a body lumen partway through the body lumen.

Accordingly, in various embodiments, a pointed tip 104 of a securing device 102 may not puncture or rupture an abluminal surface 116 of a body lumen wall 112. This may, in turn, and as discussed above, prevent fluid leakage through a lumen wall 112 as well as tissue damage to tissue external to abluminal surface 116. Additionally, a securing device 102 may be constructed to a specific dimension or size (e.g., a pointed tip 104 may be constructed to a particular length prior to placement of a depth stop) depending upon a thickness of a body lumen wall 112 into which the securing device 102 must penetrate. In other words, a securing device 102 may be designed to fit and/or be used with a variety of body lumens (each body lumen potentially having a unique thickness).

Figure 2A:
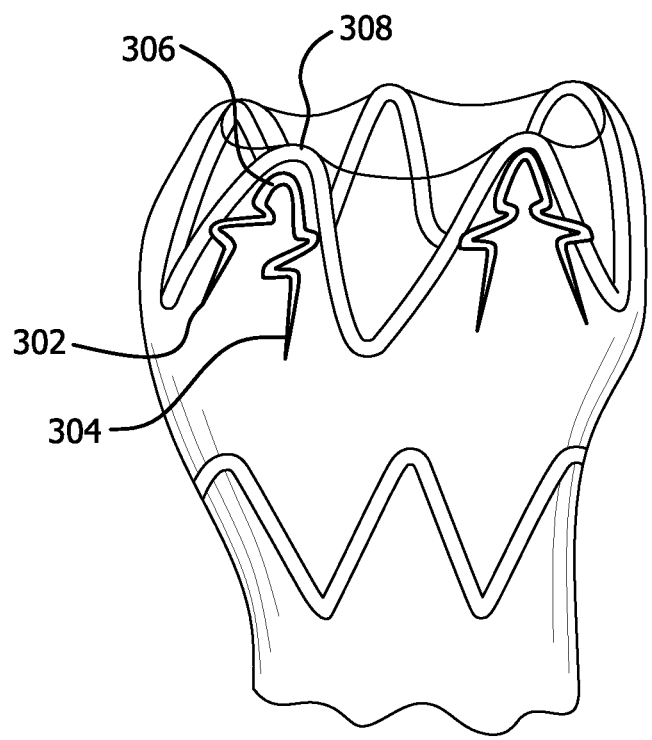
FIG. 2A illustrates a perspective view of a plurality of two pronged securing devices coupled to a medical device.

With reference to FIG. 2A, a perspective view of a two pronged device is shown. As illustrated, a two pronged device may comprise a plurality of securing devices 302 and 304. Each securing device 302 and 304 may comprise, as described above, a depth stop. Moreover, in various embodiments, a securing device in a pair of securing devices 302 and 304 may be coupled to the other securing device in the pair of securing devices, such that the pair of securing devices 302 and 304 comprises an integral two pronged device. A two pronged device may, as shown, be symmetrical about a centerline defined by a depression or trough 306 formed by the intersection of the securing devices 302 and 304. In various embodiments, a two pronged device may be formed from a length of wire, e.g., a length of shape memory wire such as a length of wire comprising Nickel Titanium alloy (or NiTi).

In various embodiments, a securing device and/or a two pronged device (hereinafter simply a "securing device" or "securing devices" for ease of reference) may be coupled to a medical device 308. Similarly, in various embodiments, a plurality of securing devices may be coupled to a medical device 308 and/or a plurality of medical devices. A securing device may be coupled to a medical device 308 by way of any method known in the art (e.g., chemical adhesion, thermal adhesion, metallurgical adhesion or bonding, integral construction with the medical device, and the like).

Figure 2B:
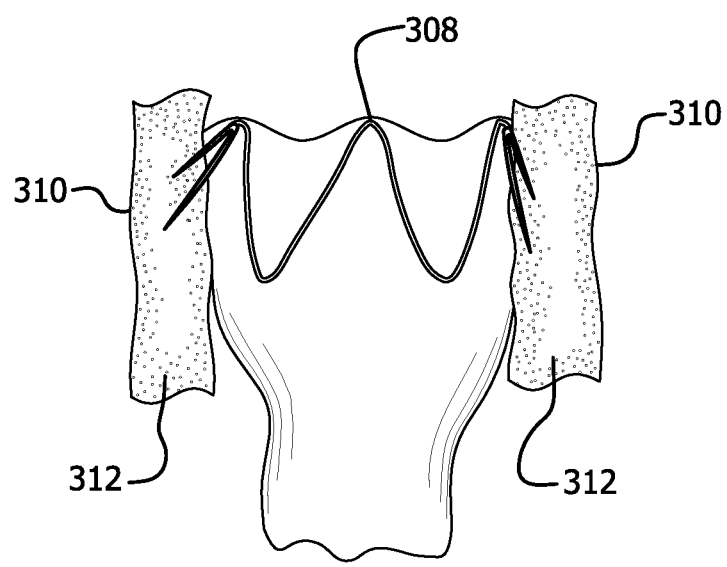
FIG. 2B illustrates a cross-sectional view of a plurality of securing devices engaged with a body lumen wall.

Referring to FIG. 2B, one or more securing devices (e.g., one or more two pronged devices) 310 may be coupled to a medical device 308 and deployed within a body lumen such that the securing devices 310 engage a body lumen wall 312. In various embodiments, a securing device may lay flat or substantially flat against a medical device 308 surface (e.g., as illustrated at FIG. 2A) until the medical device is positioned as desired (e.g., by a physician manipulating the medical device and/or a delivery lumen containing the medical device) within a body lumen. A securing device 310 may, in various embodiments, be urged into a flat position against a medical device 308 surface by a delivery sheath, which may overlay and, to some extent, compress the securing device 310 and/or the medical device 308 for delivery. A securing device 310 thus compressed may be spring loaded. Similarly, in various embodiments, a securing device 310 may adopt a flattened profile in response to a particular ambient temperature (e.g., the securing device 310 may comprise a heat sensitive shape memory alloy, which may flatten or adopt a disengaged profile during a martensite phase).

In various embodiments, a securing device 310 may be deployed with a medical device delivery system (e.g., through the working channel of a therapeutic endoscope having, for example, a diameter and/or radius less than or equal to about six millimeters, and using an everting sleeve delivery system. During deployment, one or more securing devices 310 may spring out, away from a medical device 308, such that each securing device 310 makes contact with and penetrates a body lumen wall 312. A securing device 310 may deploy in response to removal of a delivery sheath, as described above. Where a securing device 310 springs into a deployed position, the securing device 310 may do so in response to a spring loaded force, such as a natural tendency of the securing device 310 (which, again, may comprise a shape memory material), to return to a formed shape or configuration. Similarly, in various embodiments, a securing device 310 may deploy in response to being heated to a particular temperature (e.g., a typical normothermic human body temperature, which may cause the securing device 310 to enter an austenite phase). In various embodiments, a securing device 310 may make contact with a body lumen wall 312 at a variety of angles, including acute angles, a ninety degree angle, and obtuse angles.

Further, in various embodiments, a securing device 310 may penetrate, as discussed above, a body lumen wall 312 to a depth that is limited by a depth stop. Thus, a securing device may be deployed within a body lumen, such that the securing device is unable to penetrate an outer surface of a body lumen wall 312. This feature may, as described herein, protect tissue external to a body lumen wall 312 from damage by a securing device 310. This feature may also prevent a puncture or rupture of a lumen wall 312, which might result in fluid leakage between the body lumen and tissue external to the lumen.

In various embodiments, a securing device may comprise a threaded or threadable structure. Similarly, in various embodiments, a delivery lumen may comprise a threaded or threadable structure. For example, where a securing device comprises a threaded structure, the device may rotate through a threaded delivery lumen and/or deploy within a body lumen and/or body tissue in a rotating manner. Simply put, in various embodiments, a securing device may be deployed like a screw. A securing device thus deployed may incise or cut a spiraling channel within body tissue, which may aid in the secure placement of the device within the tissue.

Similarly, in various embodiments, any of the securing devices described herein may include or incorporate one or more barbs or hooks. For example, a securing device (including a barb, as discussed above) may include one or more barbs, each of which may have a pointed tip that points in a distal direction. Thus, a barbed securing device may be easily deployed within tissue but resist motion in a distal direction).

Further, in various embodiments, a plurality of securing devices may be loaded into a delivery lumen for sequential delivery within a body. These devices may be loaded within a delivery lumen in a straightened configuration and/or a substantially straightened configuration, which may facilitate delivery to body tissue in a minimally biologically invasive manner.

With brief regard to grafts and stent-grafts, many graft materials are known, and in various embodiments, these materials can be used in combination and assembled together to comprise a graft. These materials may be further extruded, coated and/or formed from wrapped films, and/or a combination thereof. Polymeric materials, biodegradable materials, and/or natural materials can be used for specific applications.

In various embodiments, a graft may comprise synthetic polymers including nylon, polyacrylamide, polycarbonate, polyformaldehyde, polymethylmethacrylate, polytetrafluoroethylene, polytrifluorochlorethylene, polyvinylchloride, polyurethane, elastomeric organosilicon polymers, polyethylene, polypropylene, polyurethane, polyglycolic acid, polyesters, polyamides, their mixtures, blends, and copolymers. In a variety of embodiments, a graft may be made from a class of polyesters such as polyethylene terephthalate including DACRON® and MYLAR® and polyaramids such as KEVLAR®, polyfluorocarbons such as polytetrafluoroethylene (PTFE) with and without copolymerized hexafluoropropylene (TEFLON® or GORE-TEX®), and porous or nonporous polyurethanes. Further, in a variety of embodiments, a graft may comprise expanded fluorocarbon polymers (especially PTFE).

In various embodiments, fluoropolymers may include polytetrafluoroethylene (PTFE), expanded PTFE (ePTFE), fluorinated ethylene propylene (FEP), copolymers of tetrafluoroethylene (TFE) and perfluoro (propyl vinyl ether) (PEA), homopolymers of polychlorotrifluoroethylene (PCTFE), and its copolymers with TFE, ethylene-chlorotrifluoroethylene (ECTFE), copolymers of ethylene-tetrafluoroethylene (ETFE), polyvinylidene fluoride (PVDF), and polyvinylfluoride (PVF). In various embodiments, a graft may comprise any combination of the materials listed above. Further, in various embodiments, a graft may be substantially impermeable and/or permeable to bodily fluids. A substantially impermeable graft may be made from materials that are substantially impermeable to bodily fluids or can be constructed from permeable materials treated or manufactured to be substantially impermeable to bodily fluids (e.g. by layering different types of materials described above or known in the art). In various embodiments, a medical device, as described above, may be made from any combination of the materials described above, including ePTFE.

Any stent may be generally cylindrical when restrained and/or when unrestrained and may comprise helically arranged undulations having a plurality of helical turns. In a variety of embodiments, undulations may be aligned so that they are "in-phase" with each other. More specifically, undulations may comprise apices in opposing first and second directions. When these undulations are in-phase, apices in adjacent helical turns are aligned so that apices can be displaced into respective apices of a corresponding undulation in an adjacent helical turn. In certain embodiments, undulations may have a sinusoidal shape, a U shape, a V shape, and/or an ovaloid shape.

In various embodiments, a stent may be fabricated from a variety of biocompatible materials including commonly known materials (or combinations of materials) used in the manufacture of implantable medical devices. Such materials may include 316L stainless steel, cobalt-chromium-nickel-molybdenum-iron alloy ("cobalt-chromium"), other cobalt alloys such as L605, tantalum, nitinol, or other biocompatible metals. In some embodiments, any stent and/or stent-graft described herein may comprise a balloon expandable stent and/or stent-graft and/or a self-expanding stent and/or stent-graft. Further, in certain embodiments, a stent may comprise a wire wound stent, which may or may not comprise undulations.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size, and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. A medical securing device coupled to a medical device that is one of a stent or a stent-graft, the medical device having a longitudinal axis, the medical securing device comprising:

a barb comprising:

a pointed tip including an elongate body having a length between a first end and a pointed end, the pointed tip terminating at the pointed end, the elongate body extending between the first end and the pointed end along a middle axis that extends perpendicular to the longitudinal axis of the medical device, the pointed tip adapted to penetrate tissue; and a depth stop extending radially outward from the medical device and defining an S-shape in a radial direction relative to the longitudinal axis of the medical device, the S-shape extending along the middle axis that extends perpendicular to the longitudinal axis of the medical device, the depth stop comprising an apex portion that is laterally offset from the middle axis in a first direction and coupled to a trough portion that is laterally offset from the middle axis in a second direction, the pointed tip extending at an angle from the depth stop and parallel to the middle axis, wherein each of the apex portion and the trough portion is capable of individually limiting a depth of penetration of the medical securing device into a body lumen wall.

2. The medical securing device of claim 1, the barb comprising a length of shape memory wire.

3. The medical securing device of claim 2, wherein the barb is configured to spring away from the medical device to which the barb is secured during deployment.

4. The medical securing device of claim 1, wherein the pointed tip is constructed to a specific length based upon a body lumen wall thickness.

5. The medical securing device of claim 1, wherein the depth stop is configured to prevent the pointed tip from fully puncturing the thickness of the body lumen wall.

6. The medical securing device of claim 1, wherein the apex portion and the trough portion form acute angles.

7. A medical device, comprising:
a stent-graft having a longitudinal axis; and
a medical securing device comprising,
 a pointed tip having a length between a first end and a pointed end and defined by an arm terminating at the pointed end, the arm extending between the first end and the pointed end along a middle axis that extends perpendicular to the longitudinal axis of the stent-graft, and
 a depth stop extending radially outward from the stent-graft and defining an S-shape in a radial direction relative to the longitudinal axis of the medical device, the S-shape extending along the middle axis that extends perpendicular to the longitudinal axis of the stent-graft, the depth stop comprising an apex portion that is laterally offset from the middle axis in a first direction and coupled to a trough portion that is laterally offset from the middle axis in a second direction,
 wherein each of the apex portion and the trough portion is configured to individually limit a depth of penetration of the medical securing device into a body lumen wall,
 wherein the trough portion is coupled to the stent-graft; and
 wherein the pointed tip extends substantially orthogonal to the longitudinal axis of the stent-graft.

8. The medical device of claim 7, wherein the apex portion extends in the first direction and the trough portion extends in the second direction opposite that of the first direction.

9. The medical device of claim 7, wherein the medical securing device comprises shape memory wire.

10. The medical device of claim 7, wherein the medical securing device is configured to spring away from the medical device during deployment.

11. The medical device of claim 7, wherein the apex portion and the trough portion form acute angles.

12. A method of securing a medical device within a body lumen, the method comprising:
 delivering a medical device to a location within the body lumen, the medical device having a longitudinal axis, the medical device being coupled to a barb, the barb comprising:
 a pointed tip including an elongate body having a length between a first end and a pointed end, the elongate body extending between the first end and the pointed end along a middle axis that extends perpendicular to the longitudinal axis of the medical device, the elongate body terminating at the pointed end, the pointed tip adapted to penetrate tissue; and
 a depth stop extending radially outward from the medical device and defining an S-shape in a radial direction relative to the longitudinal axis of the medical device, the S-shape extending along the middle axis that extends perpendicular to the longitudinal axis of the medical device, the depth stop comprising an apex portion that is laterally offset from the middle axis in a first direction and coupled to a trough portion that is laterally offset from the middle axis in a second direction, the pointed tip extending at an angle from the depth stop and parallel to the middle axis;
 deploying the barb such that the pointed tip penetrates a body lumen wall of the body lumen, wherein the trough portion limits a depth of penetration of the medical securing device into the body lumen wall by halting penetration with the apex portion extending into the tissue.

13. The method of claim 12, wherein deploying the barb comprises allowing the barb to spring away from the medical device during deployment.

14. The method of claim 12, wherein deploying the barb comprises removing a delivery sheath to allow the barb to spring away from the medical device.

15. The method of claim 12, wherein the apex portion extends in the first direction and the trough portion extends in the second direction opposite that of the first direction.

16. The method of claim 12, wherein the barb comprises a length of shape memory wire.

17. The method of claim 12, wherein the depth stop is configured to prevent the pointed tip from fully puncturing the thickness of the body lumen wall.

18. The method of claim 12, wherein the medical device is a stent-graft.

19. The method of claim 12, wherein the medical device is a stent.

20. The method of claim 12, wherein locating the medical device within the body lumen comprises delivering the medical device coupled to the barb through a therapeutic endoscope.

21. The method of claim 12, wherein the apex portion and the trough portion form acute angles.

* * * * *